United States Patent
Rasmussen

(10) Patent No.: US 6,935,860 B2
(45) Date of Patent: Aug. 30, 2005

(54) APPARATUS FOR DENTAL ABRASIVE TREATMENT OF TEETH

(75) Inventor: Ove Peter Rasmussen, Klarup (DK)

(73) Assignee: Sandman ApS, Aalborg (DK)

( * ) Notice: Subject to any disclaimer, the term of this patent is extended or adjusted under 35 U.S.C. 154(b) by 0 days.

(21) Appl. No.: 10/395,836

(22) Filed: Mar. 25, 2003

(65) Prior Publication Data

US 2003/0219695 A1 Nov. 27, 2003

Related U.S. Application Data

(63) Continuation of application No. PCT/DK01/00619, filed on Sep. 27, 2001.

(30) Foreign Application Priority Data

Sep. 27, 2000 (DK) .......................................... 2000 01422
Jan. 12, 2001 (DK) .......................................... 2001 00044

(51) Int. Cl.$^7$ ................................................. A61C 3/02
(52) U.S. Cl. ....................................................... 433/88
(58) Field of Search ......................... 451/102; 222/566; 433/88

(56) References Cited

U.S. PATENT DOCUMENTS

| 2,759,266 A | * | 8/1956 | Cassani ........................ 433/88 |
| 4,057,938 A | * | 11/1977 | Rohlfs ......................... 451/92 |
| 4,067,150 A | * | 1/1978 | Merrigan ...................... 451/99 |
| 4,482,322 A | | 11/1984 | Hain et al. |
| 6,325,624 B1 | * | 12/2001 | Kutsch et al. ................. 433/88 |

FOREIGN PATENT DOCUMENTS

| EP | 0 858 783 | 8/1998 |
| WO | WO 97/06924 | 2/1997 |
| WO | WO 00/21452 | 4/2000 |

OTHER PUBLICATIONS

International Search Report dated Jan. 2, 2002 form International Application No. PCT/DK01/00619.

* cited by examiner

Primary Examiner—Cary E. O'Connor
(74) Attorney, Agent, or Firm—Nixon Peabody LLP; David S. Safran

(57) ABSTRACT

The invention relates to apparatuses for treating surfaces of teeth by using a mixture of pressurised gas, preferably pressurised air, and abrasive particles such as particles of aluminium oxide. A first apparatus comprises a chamber having at least a primary inlet and preferably an additional inlet and also having an outlet. The primary inlet establishes a vortex within the chamber and the additional inlet fluidises the abrasive particles lying in the bottom of the chamber. A second apparatus comprises a handpiece with a nozzle having an outlet provided with notches or holes. The notches or holes constitute additional discharge openings apart from an orifice in the nozzle. Both of the apparatuses ensure that the pressure needed for the treatment and the amount of abrasive particles for the treatment is minimised as much as possible.

19 Claims, 4 Drawing Sheets

APPARATUS FOR DENTAL ABRASIVE TREATMENT OF TEETH

The present invention relates to an apparatus for dental abrasive treatment of teeth, said apparatus having a chamber for mixing pressurised gas with abrasive particles. The invention also relates to an apparatus having both a chamber for mixing pressurised gas with abrasive particles and a hand piece with additional outlets apart from an orifice for the mixture of gas and particles. Finally, the invention also relates to an apparatus for dental abrasive treatment of teeth, said apparatus having a hand piece with additional outlets apart from an orifice for the mixture of gas and particles.

BACKGROUND OF THE INVENTION

U.S. Pat. No. 6,083,001 describes an apparatus for accurate control of particles flow with regard to feeding abrasive material to a surface of teeth during dental treatment. The apparatus comprises a compressor for establishing a flow of pressurised air, a chamber for mixing the pressurised air and the particles of abrasive material and a hand piece for letting out the mixture of pressurised air and abrasive material onto the surface of the teeth, which are to be treated. The chamber for mixing the pressurised air and the particles of abrasive material has an inlet for pressurised air, said inlet being situated in an outlet for the abrasive material at a level below a top level of abrasive material in the chamber. Thus, the mixing of pressurised air and particles of abrasive material takes place directly at the outlet of the abrasive material towards the hand piece.

This, however, has the disadvantage that the mixing of the pressurised air and the particles of abrasive material only has very little time and very little space during which and in which the mixing can take place. This results in either an unsatisfactory mixing and/or a very uneven mixing of the pressurised air and the particles of abrasive material.

U.S. Pat. No. 6,004,191 describes a hand piece where mixing of pressurised air and particles of abrasive material takes place in a chamber in the hand piece itself and where a fluidisation of the particles of abrasive material is established during mixing. The pressurised air is let into the chamber along a tube extending from one end towards another end of the chamber and with an orifice directed towards the other end. The mixed pressurised air and particles of abrasive material are let out of the chamber through another tube extending from a position in the middle of the chamber and towards and out through the other end of the chamber. This apparatus ensures a mixing which fluidises the particles of abrasive material.

However, still the mixing may be unsatisfactory or may be very unequal due to the pressurised air being let towards the other end of the chamber. This results in the mixing being very dependent on the amount of particles of abrasive material which is present in the chamber, and also being very dependent on the inclination of the chamber and thus where in the chamber that the particles of abrasive material is situated.

U.S. Pat. No. 4,482,322 describes a device for mixing an abradant with pressurised gas. The device comprises a reservoir for the abradant and a separate vortex chamber for mixing the abradant and the pressurised gas. An inlet in the vortex chamber is provided tangentially to the circumference of the chamber so that air flowing into the vortex chamber is swirled in a controlled manner. Thereby a favourable swirling of the abradant is obtained. An orifice is provided in the bottom of the reservoir, and the abradant is thus intended, by means of gravity, for trickling down into the vortex chamber through the orifice. The trickling down is provided by vibrating the reservoir.

As mentioned, the device comprises a reservoir for containing the abradant and a separate vortex chamber for mixing the abradant with pressurised gas just before being used for surface treatment of teeth. For passing the abradant to the vortex chamber through the orifice, means has to be provided for vibrating the reservoir. This makes the device expensive and technically complicated and increases the need for regulation and adjustment means for obtaining correct dosage of the abradant and correct mixing of the abradant with the pressurised gas.

It is an object of the present invention to provide an apparatus, which ensures not only a satisfactory mixing of pressurised air and particles of abrasive material, but which also ensures a very equal distribution of the particles in the air so that a thorough and uniform abrasive treatment of the surfaces of teeth may be obtained together with an apparatus not comprising technically complicated and economically cost increasing means.

BRIEF DESCRIPTION OF THE INVENTION

This object is obtained by one embodiment of the apparatus, where the apparatus comprises a hand piece, a means for establishing a flow of pressurised gas, and a chamber for mixing said pressurised gas with abrasive particles, said chamber having a circular cross-section and a bottom being intended for containing an amount of abrasive particles, and said chamber comprising a primary inlet for the pressurised gas, and an outlet for a mixture of pressurised gas and abrasive particles, and the inlet extending along a tube or a pipe from outside of the chamber into the interior of the chamber and having an orifice directed tangentially to the circular cross-section, and said chamber furthermore comprising an additional inlet for pressurised air.

By combining a flow of gas, preferably a flow of air, which is directed tangentially to a cross-section of the chamber, and an additional inlet of pressurised air, the abrasive material is blown up into the chamber by means of the additional inlet and a vortex of gas and abrasive particles is established in the chamber by means of the primary inlet.

Then a very uniform, but also thorough, mixing of the pressurised gas and the abrasive particles is accomplished. The effect is that not only is the dental treatment taking place in a very uniform and accurate way, but also the gas pressure needed for still obtaining this very satisfactory treatment is limited. Thus, the means for establishing the pressurised gas may be smaller than if not using the present invention. A smaller means for establishing the pressurised gas results in less noise which is environmentally desirable in a dental clinic, but which also reduces the fear of many people of visiting the dentist. The even and thorough mixing of the pressurised gas and the abrasive particles also reduces the amount of abrasive particles to be used.

In a preferred embodiment the additional inlet for pressurised air is extending along a tube from outside of the chamber into the interior of the chamber and is having an orifice being situated in the amount of abrasive particles, and thus below the top surface of the amount of abrasive particles in the bottom of the chamber.

By providing the additional inlet having an orifice in the amount of abrasive particles, the certainty is enhanced of particles being blown up into the void of the chamber, the void where the primary inlet is establishing a vortex. Thus, it is not the primary inlet itself, which has the task of both blowing the abrasive particles up into the chamber and also establishing the vortex of fluidised abrasive particles. Therefore, the task of establishing the vortex may be optimised by utilising the primary inlet, and the task of fluidising the abrasive particles may also be optimised by utilising the additional inlet. Thus, both the primary inlet and the additional inlet only have one task to perform, and which task therefore may be optimised without having to enter into compromises because of the need of multiple tasks.

In another embodiment of the apparatus, the apparatus comprises a hand piece, a means for establishing a flow of pressurised gas, and a chamber for mixing said pressurised gas with abrasive particles, said hand piece having a nozzle with an outlet, and said outlet having an orifice providing a discharge opening for the mixture of pressurised gas and abrasive particles, said outlet furthermore being provided with a number of notches or a number of holes, and said number of notches or holes establishing additional discharge openings, apart from the orifice, for the mixture of pressurised gas and abrasive particles.

It is has been discovered that the dental treatment not only depends on the correct, accurate and thorough mixing of the pressurised gas and abrasive particles, but is also very and perhaps even more dependent on the manual handling by the dentist of the hand piece of the apparatus. If the dentist holds the hand piece, and thus the orifice of the hand piece, far from the tooth surface to be treated, it may take longer time for the surface to be treated. This results in an increase in the amount of abrasive particles being used for treating the surface, but it also results in the patient having to endure a longer treatment. This is a disadvantage, but is also more costly, because the dentist cannot treat so many patients when each treatment takes a prolonged period of time.

On the other hand, if the dentist holds the hand piece too near the tooth surface to be treated, it may take a shorter time to treat the surface, but the result is an increased risk of damaging the surface of the tooth and the neighbouring gum. Also, it may be more painful than necessary for the patient to be treated. Thus, holding the orifice of the hand piece closer to the tooth surface to be treated is also a disadvantage.

By providing a number of notches or holes in the nozzle of the hand piece, and which number of notches or holes establishes additional discharge openings apart from the orifice of the nozzle, it is possible to let the orifice abut the tooth surface to be treated. By having the possibility of letting the orifice abut the tooth surface, the proper distance from the tooth surface to hold the orifice of the hand piece is easily obtained without having to think about whether the distance is too far or too near. Some of the mixture of pressurised gas and abrasive particles will be let out through the orifice for treating the tooth surface. However, the rest of the mixture of pressurised gas and abrasive particles will be let out through the additional discharge openings, and will not be used for treating the tooth surface. However, the discharge of superfluous mixture of pressurised gas and abrasive particles will reduce the risk of a "not proper" or a "too proper" treatment of the tooth surface. The correct and accurate dosage of pressurised gas and abrasive particles may be obtained by using a certain nozzle having a certain number of notches or holes and having a certain shape of the notches or holes.

In a preferred embodiment the apparatus comprises a chamber having a primary inlet for the pressurised gas, and an outlet for a mixture of pressurised gas and abrasive particles, the inlet extending along a tube or a pipe from outside of the chamber into the interior of the chamber and having an orifice directed tangentially to the circular cross-section, and the apparatus also comprises a hand piece having a nozzle with an outlet, said outlet having an orifice providing a discharge opening for the mixture of pressurised gas and abrasive particles, said outlet furthermore being provided with a number of notches, and said number of notches establishing additional discharge openings, apart from the orifice, for the mixture of pressurised gas and abrasive particles.

By combining the apparatus with a chamber according to the invention and with a hand piece according to the invention, a synergetic effect is obtained. Not only is mixture of pressurised gas and abrasive particles optimal, but also the discharge of the mixture is optimal. Accordingly, both the treating means for treating the tooth surface and the treatment itself are as good as can be obtained, and these two effects in combination result in the treatment at one and same time being as material-saving, as time-saving and as cost-saving as possible.

BRIEF DESCRIPTION OF THE FIGURES

The invention will now be described further with reference to the accompanying drawing, where.

DETAILED DESCRIPTION OF THE INVENTION

Figure 1:
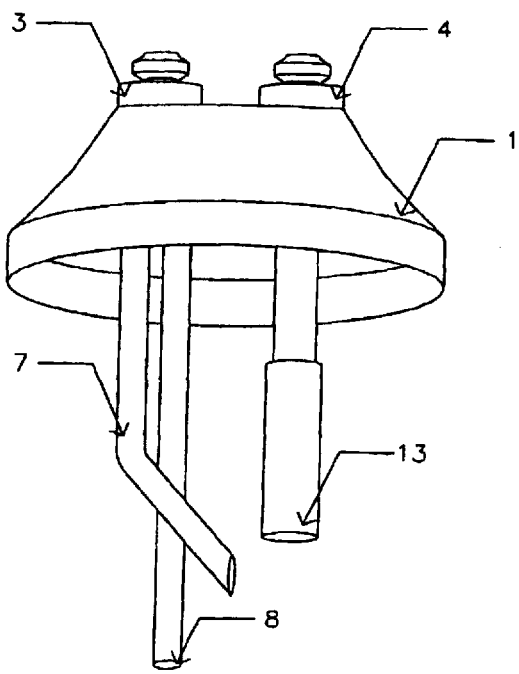
FIG. 1 is a picture being a perspective view of an embodiment of inlets and an outlet in a top of a chamber for an apparatus according to the invention.

FIGS. 1–4 are a picture and drawings showing a top 1 for a chamber and container 2 (see FIG. 3) for the chamber itself and to be utilised in an apparatus for dental abrasive treatment of teeth. The top is frusto-conical and is provided with an exterior inlet 3 and an exterior outlet 4. The container 2 (see FIG. 3) enclosing the chamber is circular cylindrical at an upper part 5 of the container and is semi-spherically shaped at a lower part 6 of the container, said lower part constituting a bottom of the chamber. The lower part 6 of the container and thus of the chamber is intended for containing abrasive particles (not shown) to be used during the dental abrasive treatment of the teeth. The abrasive particles are preferably particles of aluminium oxide, but other particles suitable for the abrasive treatment may be used.

Figure 2:
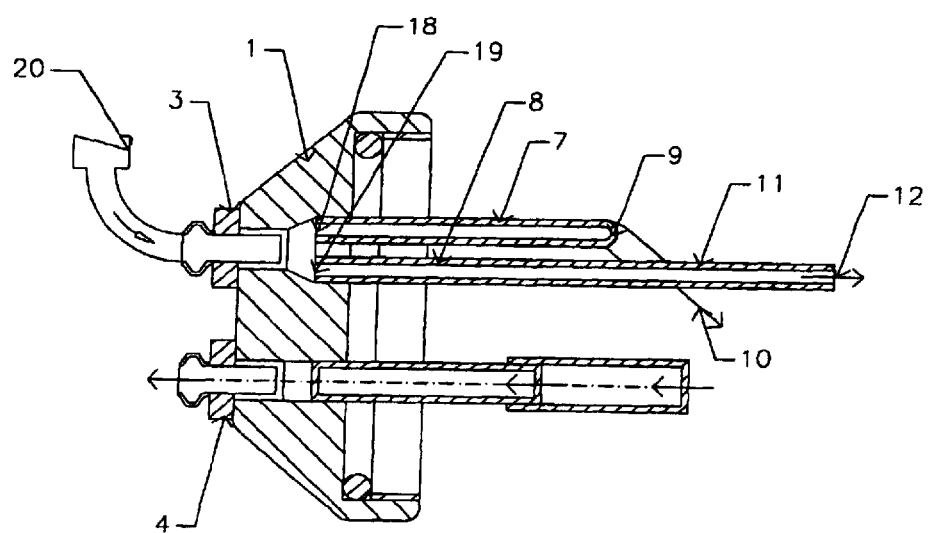
FIG. 2 is a drawing being a cross-section of the embodiment of inlets and the outlet in the top of the chamber for the apparatus according to the invention.
Figure 3:
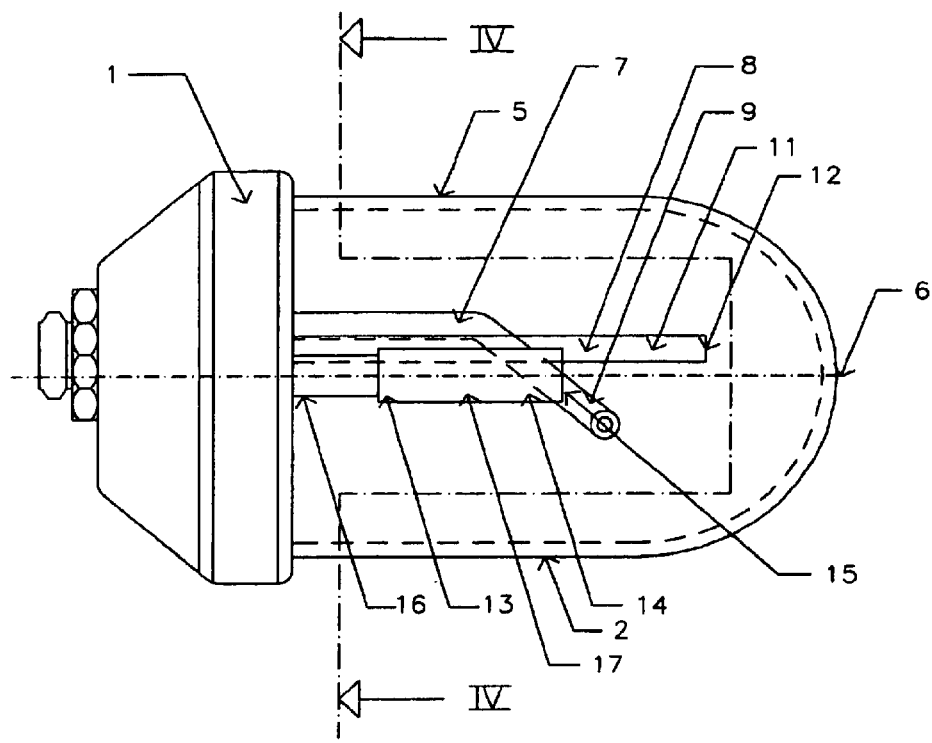
FIG. 3 is a drawing being a side plane view of the embodiment of inlets and the outlet in the top and the chamber itself for the apparatus according to the invention.
Figure 4:
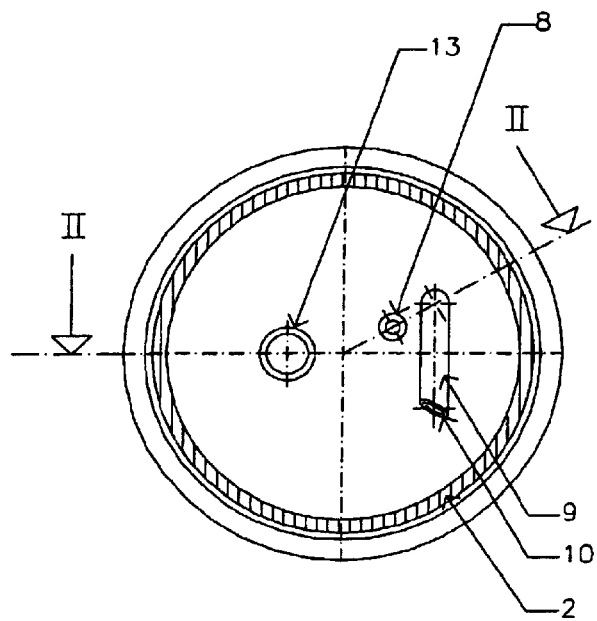
FIG. 4 is a drawing being a bottom plane view of the embodiment of inlets and the outlet in the top of the chamber for the apparatus according to the invention.

The exterior inlet divides into an interior primary inlet 7 and an interior additional inlet 8 (see FIG. 2). The primary inlet 7 extends along a pipe from the top 1 towards the bottom of the chamber. An outer end 9 of the pipe is bent sideways and downwards and is having an orifice 10 directed tangentially to a circumference of the circular cross-section of the chamber. Due to the sideways bending of the primary inlet, a vortex is established when pressurised air is let into the chamber through the primary inlet 7. Due to the downward bending, the vortex is established from a lower part of the chamber and upward towards the top of the chamber. The orifice 10 of the primary inlet 7 is arranged so that it falls into a level above an intended level of a top surface of the abrasive particles lying in the bottom of the chamber. However, alternatively it will be possible to let the orifice 10 fall into a level just beneath the top surface of the abrasive particles lying in the bottom of the chamber.

The additional inlet 8 also extends along a pipe from the top 1 towards the bottom of the chamber. An outer end 11 of the pipe is directed downwards and is having an orifice 12 directed into a plane parallel to the circular cross-section of the chamber. The orifice of the additional inlet 8 is arranged so that it falls into a level beneath the intended level of a top surface of the abrasive particles lying in the bottom of the chamber. However, alternatively it will be possible to let the orifice fall into a level just above the top surface of the abrasive particles lying in the bottom of the chamber. The additional inlet 8 is optional and, as mentioned, is intended for blowing up the abrasive particles lying in the bottom of the chamber. Thus, the additional inlet 8 is fluidising the abrasive particles and the primary inlet 7 is creating a vortex of the fluidised abrasive particles in the pressurised air.

An interior outlet 13 also extends along a pipe from a position in the middle of the chamber and to the top 1 of the chamber to the exterior outlet 4 of the chamber. An outer end 14 of the pipe is directed downwards and is having an orifice 15 directed into a plane parallel to the circular cross-section of the chamber. The orifice 15 of the outlet 13 is arranged so that it falls into a level above the intended level of a top surface of the abrasive particles lying in the bottom of the chamber.

The pipe is arranged telescopically by providing an inner fixed pipe 16 with an outer displaceable sleeve 17, so that the orifice 15 may be arranged in different levels within the chamber. Thus, it is possible to adjust where in the vortex of pressurised air and abrasive particles that the mixture of these two items is to be let out of the chamber. Accordingly, by sliding the outer sleeve 17 downwards or upwards in relation to the fixed pipe 16, the orifice 15 of the outlet 13 will be positioned at a lower level or at a higher level, respectively, and the position in the vortex where the mixture is extracted from the chamber through the outlet 13 will alter accordingly. This may advantageously depend on the type of abrasive particles used, the particle size of the abrasive particles, the magnitude of pressure of the pressurised air, the remaining amount of abrasive particles in the bottom of the chamber and perhaps other factors influencing the vortex. However, alternatively it will be possible to let the orifice fall into a level just above the top surface of the abrasive particles lying in the bottom of the chamber.

The container 2 constituting—together with the top 1—the boundaries of the chamber are preferably made of glass or other transparent and abrasive resistant material. Thereby it is possible to visually determine the amount of abrasive particles left in the chamber. However, in order to ensure a proper wear resistant container without using glass, the container may be made of other materials, preferably metal, and the amount of abrasive particles have to be determined by de-mounting the container 2 from the top 1 of the chamber. The top 1 is preferably made of metal, and more preferably made of aluminium.

As shown in FIG. 2, in the top 1 of the chamber the exterior inlet 3 is divided into two interior initial inlets 18, 19, each leading to the primary inlet and the additional inlet, respectively, as mentioned above. The division into the two initial inlets 18, 19 is taking place in the top 1 itself. The exterior inlet 3 is divided so that the amount of pressurised air being let to the exterior inlet 3 is divided equally between the two initial interior inlets 18, 19. This is accomplished by having the division shaped as a sort of fork as shown. Thereby, there is no risk of either the primary inlet 7 or the additional inlet 8 being provided with more pressurised air at the expense of the other inlet.

Also, as shown in FIG. 2, all the different parts in the top of the chamber, i.e. the exterior inlet 3, the exterior outlet 4, the interior inlets 7,8, the interior outlet 13 and the top 1 itself are provided with threads. Thereby, each of the individual parts of the top 1 may be replaced if needed because of wear, failures or because of a need for any of these parts having other dimensions than the ones of the originally fitted parts. The exterior inlet 3 and the exterior outlet 4 are preferably provided with quick-fit couplings for connecting the inlet 3 and the outlet 4 with hoses or pipes from the means for establishing the pressurised air (not shown) and to the hand piece (see FIG. 8) of the apparatus, respectively. The exterior inlet 3 is preferably provided with a check valve 20 arranged between the means (not shown) for establishing the pressurised air and the exterior inlet 3 itself. Thus, there is no risk of abrasive particles accidentally being led backwards to the means for establishing the pressurised air and damaging this means.

The dimensions of the individual parts may vary dependent on the intended capacity of the apparatus, the possible already available plant for establishing pressurised air and other specific factors which may influence the choice of dimensions. In the following a possible selection of dimensions which have proven to be efficient is listed.

| | |
|---|---|
| Inner diameter of primary inlet pipe | 2.0 mm |
| Inner diameter of additional inlet pipe | 2.0 mm |
| Inner diameter of outlet fixed pipe | 4.0 mm |
| Inner diameter of outlet sleeve | 6.0 mm |
| Inner diameter of chamber | 49.0 mm |
| Distance from centre of chamber to primary inlet | 13.0 mm |
| Distance from centre of chamber to additional inlet | 7.5 mm |
| Distance from centre of chamber to outlet | 7.5 mm |
| Distance from interior of top to interior of bottom | 80.0 mm |
| Distance from primary inlet orifice to bottom | 25.0 mm |
| Distance from additional inlet orifice to bottom | 15.0 mm |
| Distance (max.) from outlet orifice to bottom | 54.0 mm |
| Distance (min.) from outlet orifice to bottom | 34.0 mm |

The pressure of the pressurised air being let to the exterior inlet is between 20 psi and 80 psi, preferably between 30 psi and 60 psi, more preferably between 40 psi and 50 psi, even more preferably 45 psi. These pressures have shown to provide adequate abrasive force to the treatments of the teeth, although these pressures are relatively low.

Figure 5:
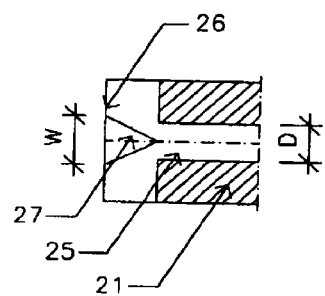
FIG. 5 is a cross-section of an outlet of a nozzle of a hand piece for an apparatus according to the invention.
Figure 6:
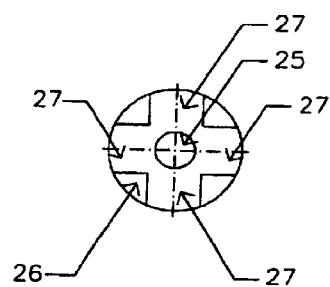
FIG. 6 is a bottom plane view of the outlet of the nozzle of the hand piece for the apparatus according to the invention.

FIGS. 5–6 are drawings showing a nozzle 21 for a hand-piece (see FIG. 8) for an apparatus according to the invention. FIG. 5 is a cross-sectional view along a longitudinal axis A of an embodiment of a nozzle 21. FIG. 6 is a plane view seen from beneath of an outlet of the nozzle 21.

Figure 7:
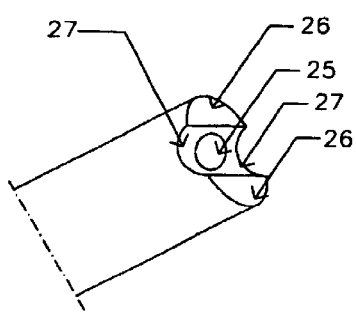
FIG. 7 is a picture being a perspective view of an embodiment of a nozzle of the hand piece for the apparatus according to the invention.
Figure 8:
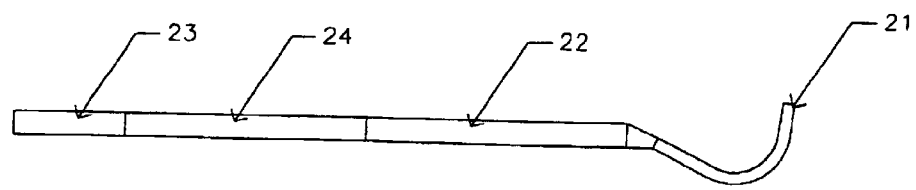
FIG. 8 is a picture being a perspective view of an embodiment of a hand piece with a handgrip and a nozzle and for an apparatus according to the invention.

FIG. 7 is a picture showing a possible embodiment of an outlet of a nozzle. FIG. 8 is a picture showing a complete hand-piece 22 for an apparatus according to the invention. The hand-piece 22 consists of a distant end 23 for connecting the handpiece to pressurised air mixed with abrasive particles, a handgrip 24 and a nozzle 22.

The nozzle 21 consists of a pipe having an orifice 25 for letting out a mixture of pressurised air and abrasive particles. The nozzle 21 also has sidewalls 26 provided with notches 27 made in immediate vicinity of the orifice 25. In FIG. 5 the notches 27 are shown as triangular shaped notches with the base of the triangle situated towards the orifice 25. In other embodiments the notches may have other shapes such as rectangular, oval, partly circular, semicircular or even other shapes. In the embodiment shown in FIG. 5, the notches extend along the same width w as the orifice itself, i.e. the nozzles 21 have the same lateral extension as an inner diameter d of the outlet of the nozzle 21. However, in other embodiments the lateral extension of the notches may be greater or smaller than the inner diameter of the outlet.

The notches constitute additional discharge openings apart from the orifice itself for the mixture of pressurised air and abrasive particles. The additional discharge openings constitute a kind of safety openings towards unintended too cautious or too violent treatment of the teeth. If the outlet of a common known nozzle is held in a position too far from a tooth surface to be treated, the treatment is too cautious. However, if the outlet of a common known nozzle is held in a position too near the tooth surface to be treated, the treatment is too violent. By providing notches, it is possible to let the outer lateral surfaces of the outlet, i.e. the surfaces surrounding the orifice, abut the tooth surface. Thereby, the position of the outlet is determined by a firm abutment with the tooth surface, so that the dentist does not have to worry about holding the outlet in the correct position. The notches constituting the additional discharge openings ensure that the treatment will not be too violent in respect of the actual treatment needed. By direct contact between the tooth surface and the outer end of the nozzle, the notches allow the dentist to work more precisely.

FIG. 6 shows that the embodiment of the nozzle is provided with four notches arranged oppositely along diameters of the outlet. By providing an even number of notches arranged opposite each other in pairs, it is possible to easily manufacture the notches. A cutting tool may be employed and a mutual displacement towards each other of the nozzle and the cutting tool will provide the notches. In the case of triangular notches as the ones shown in FIG. 5 or oval or rectangular notches, the cutting tool may be a file. If the notches are partly circular such as semicircular (see FIG. 7) the cutting tool may be a drill or a milling tool. Below is a list of possible dimensions of the outlet of the nozzle and of the notches for individual uses. The individual dimensions depend on the pressure of the pressurised air, on the size of the abrasive particles such as either 50 μm or 25 μm and of the actual surface treatment of the teeth in question.

| Shape of notch | Outer diameter of nozzle | Inner diameter of nozzle | Lateral width of notch (max.) | Vertical height of notch (max.) |
|---|---|---|---|---|
| Triangular | 2.00 mm | 0.65 mm | 0.80 mm | 0.80 mm |
| | 1.60 mm | 0.40 mm | 0.45 mm | 0.45 mm |
| Partly circular | 2.00 mm | 0.65 mm | 0.70 mm | 0.70 mm |
| | 1.60 mm | 0.40 mm | 0.40 mm | 0.40 mm |

Alternatively to providing notches extending from the orifice and upward along the sidewalls of the nozzle, it will be possible to provide the sidewalls of the nozzle with holes instead. Thereby, the additional discharge openings will be situated further away from the orifice of the nozzle. The risk of abrasive particles discharged through the notches unintendedly assisting in the treatment of the tooth surface is eliminated.

In the above tables, specific dimensions are stated. However, other dimensions may be employed fulfilling the same needs and demands for a proper and adequate dental abrasive treatment of teeth requiring a minimum of pressure and a minimum consumption of abrasive particles.

Figure 9:
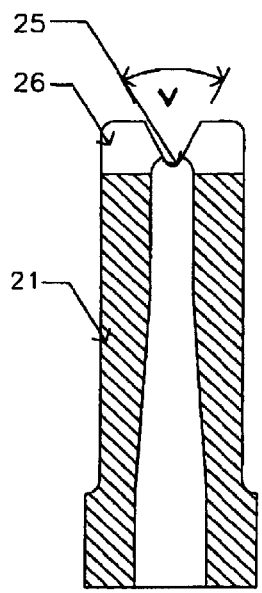
FIG. 9 is a longitudinal cross section of a possible embodiment of the nozzle.
Figure 10A:
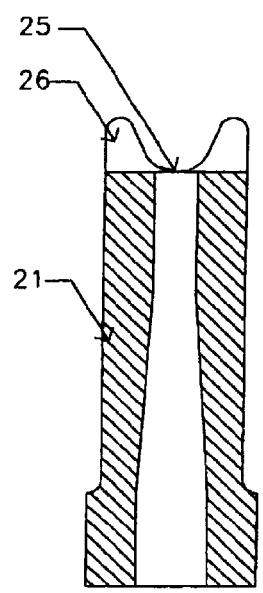
FIG. 10 is a longitudinal cross section of a further improved nozzle.
Figure 10B:
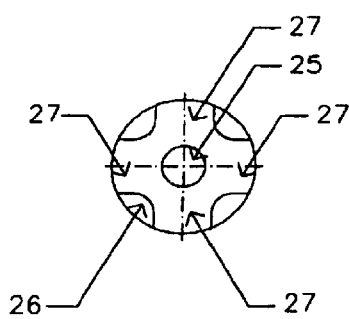

For example, a specific embodiment has turned out to be highly effective for teeth treatment. In FIG. 9 an embodiment of the nozzle 21 is shown in a longidudinal cross-sectional view, where the nozzle 21 is provided with wedge shaped notches 27, the angle v for the associated wedge is preferably 40–45 degrees. An improvement towards higher efficiency has been achieved by rounding the side walls 26 of the notches 27 in the direction towards the orifice 25, which is illustrated in FIG. 10a. The etches may, for example, be rounded by applying a drill, for example a diamond drill, with the rotational axis coinciding with the longitudinal axis of the nozzle 21.

What is claimed is:

1. An apparatus for dental abrasive treatment of teeth, said apparatus comprising a hand piece, a means for establishing a flow of pressurised gas, and a chamber for mixing said pressurised gas with abrasive particles, said chamber having a top and a bottom, and sidewalls between said top and said bottom, said sidewalls having a circular cross-section and the bottom being intended for containing an amount of abrasive particles, and said chamber comprising a primary inlet for the pressurised gas, and an outlet for a mixture of pressurised gas and abrasive particles, the outlet extending to the exterior of the chamber, and the inlet extending along a tube or a pipe from outside of the chamber into the interior of the chamber and having an orifice directed tangentially to the circular cross-section for creating a vortex of particles in the chamber, and said chamber furthermore comprising an additional inlet for pressurised air, wherein the outlet has an orifice positioned in a vortex region of the chamber for extraction of particles directly from the vortex to the exterior.

2. An apparatus according to claim 1, said primary inlet extending from the top of the chamber into the chamber towards the bottom of the chamber along a longitudinal direction being parallel with a longitudinal axis between the top and the bottom of the chamber and being perpendicular to cross-sectional planes of the chamber, and the orifice of the inlet being bent from the longitudinal direction along a curve to a transverse direction in a cross-sectional plane.

3. An apparatus according to claim 2, said primary inlet extending in a plane parallel with the cross-sections and said plane extending above the amount of abrasive particles and in the immediate vicinity of a top surface of the amount of abrasive particles in the bottom of the chamber.

4. An apparatus according claim 3, said outlet extending along a tube or a pipe from the interior of the chamber to the outside of the chamber and having an orifice directed substantially parallel to the circular cross-section.

5. An apparatus according claim 4, said outlet extending in a plane perpendicular to the cross-sections and said outlet having an orifice being situated outside the amount of abrasive particles and remote from the top surface of the amount of abrasive particles in the bottom of the chamber.

6. An apparatus according to claim 1, said additional inlet for pressurised air extending along a tube from outside of the chamber into the interior of the chamber and having an orifice being situated in the amount of abrasive particles, and thus below the top surface of the amount of abrasive particles in the bottom of the chamber.

7. Apparatus according to claim 6, where the primary inlet and the additional inlet share a common conduit for pressurised gas from the means for establishing the pressurised gas.

8. Apparatus according to claim 7, said common conduit being divided from a main conduit to a branched conduit with one branch leading to the primary conduit and another branch leading to the additional inlet, and said branches of the conduit being divided so that the branches of the conduit extend parallel in between the main conduit and the inlets.

9. Apparatus according to claim 8, the length of and the shape of the extension of each of the branches being substantially identical between the main conduit and the inlets.

10. Apparatus according to claim 1, said pressurised gas when being let to the interior of the chamber having a pressure of between 20 psi and 80 psi.

11. An apparatus according to claim 10, said pressurised gas when being let to the interior of the chamber having a pressure of between 30 psi and 60 psi.

12. An apparatus according to claim 10, said pressurised gas being fed to the interior of the chamber at a pressure of between 40 psi and 50 psi.

13. An apparatus according to claim 1, said hand piece having a nozzle with an outlet, and said outlet having an orifice providing a discharge opening for the mixture of pressurised gas and abrasive particles, said outlet furthermore being provided with a number of notches or holes, or both, said number of notches or holes establishing additional discharge openings, apart from the orifice, for the mixture of pressurised gas and abrasive particles.

14. An apparatus according to claim 13, said number of notches being provided along the circumference of the orifice and having a substantially circular shape, a substantially triangular shape, a trapezium shape, or a rectangular shape.

15. An apparatus according to claim 14, said number of notches being an even number of notches being positioned along diameters in a plane being perpendicular to a longitudinal direction of the mouth piece.

16. An apparatus according to claim 13, said number of holes being provided along the circumference of the orifice and being substantially cylindrical, conical, funnel-shaped or cup-shaped.

17. An apparatus according to claim 16, said number of holes being an even or uneven number of holes being positioned along diameters in a plane being perpendicular to a longitudinal direction of the mouth piece.

18. An apparatus according to claim 1, wherein the orifice of the outlet is directed downwards for receiving particles from the vortex.

19. An apparatus according to claim 1, wherein said additional inlet is directed axially for fluidizing the particles and has an outlet located below the tangentially directed orifice of the primary inlet.

* * * * *